United States Patent
Choi et al.

(10) Patent No.: US 8,541,620 B2
(45) Date of Patent: Sep. 24, 2013

(54) METHOD FOR SELECTIVELY CRYSTALLIZING A Z ISOMER OF IOPROMIDE

(75) Inventors: Soo-Jin Choi, Yongin-si (KR); Byung-Goo Lee, Suwon-si (KR); Han-Kuk Lee, Yongin-si (KR); Young-Mook Lim, Seongnam-si (KR); Wol-Young Kim, Seongnam-si (KR); Joon-Hwan Lee, Yongin-si (KR)

(73) Assignee: Daewoong Pharmaceutical Co., Ltd., Sungnam-si (KR)

( * ) Notice: Subject to any disclaimer, the term of this patent is extended or adjusted under 35 U.S.C. 154(b) by 165 days.

(21) Appl. No.: 13/132,791

(22) PCT Filed: Oct. 21, 2009

(86) PCT No.: PCT/KR2009/005827
§ 371 (c)(1), (2), (4) Date: Jun. 3, 2011

(87) PCT Pub. No.: WO2010/064785
PCT Pub. Date: Jun. 10, 2010

(65) Prior Publication Data
US 2011/0245347 A1    Oct. 6, 2011

(30) Foreign Application Priority Data
Dec. 5, 2008 (KR) .................. 10-2008-0123138
Sep. 9, 2009 (KR) .................. 10-2009-0085014

(51) Int. Cl.
*C07C 233/65* (2006.01)
*C07C 233/05* (2006.01)
*A61K 31/16* (2006.01)

(52) U.S. Cl.
USPC ........................................ 564/153; 514/616

(58) Field of Classification Search
USPC ........................................ 564/153; 514/616
See application file for complete search history.

(56) References Cited

U.S. PATENT DOCUMENTS
2007/0265470 A1    11/2007    Kagerer et al.

FOREIGN PATENT DOCUMENTS

| GB | 2 280 436 A | 2/1995 |
|---|---|---|
| JP | 2011-518878 A | 6/2011 |
| WO | 99/18054 A1 | 4/1999 |
| WO | 2007/013815 A1 | 2/2007 |
| WO | 2007/013816 A1 | 2/2007 |
| WO | WO 2007/065534 * | 6/2007 |
| WO | 2009/134030 A1 | 11/2009 |

OTHER PUBLICATIONS

European Patent Office, Supplementary European Search Report issued in corresponding EP Application No. 09 83 0523, dated Mar. 13, 2012.
WIPO IB, International Search Report for PCT/KR2009/005827 dated May 2010.
Japanese Patent Office, Japanese Office Action issued in corresponding JP Application No. 2011-539442, dated Mar. 19, 2013.

* cited by examiner

*Primary Examiner* — Shailendra Kumar
(74) *Attorney, Agent, or Firm* — Sughrue Mion, PLLC

(57) ABSTRACT

The present invention relates to a method for selectively crystallizing Z isomer of iopromide of formula (I) comprising a) dissolving a crude iopromide comprising a mixture of E and Z isomers or a concentrate thereof in an alcohol, and b) heating the resulting alcohol solution to obtain crystalline of Z isomer of iopromide; and a method for preparing a composition comprising the crystalline Z isomer of iopromide.

12 Claims, 2 Drawing Sheets

METHOD FOR SELECTIVELY CRYSTALLIZING A Z ISOMER OF IOPROMIDE

This application is a 371 of PCT/KR09/05827, filed Oct. 12, 2009.

FIELD OF THE INVENTION

The present invention relates to a method for selectively crystallizing a Z form isomer of iopromide from a crude crystal of iopromide comprising a mixture of E and Z iopromide isomers, and a composition comprising the Z iopromide isomer prepared by said method.

BACKGROUND OF THE INVENTION

Iopromide, 5-methoxyacetylamino-2,4,6-triiodo-isophthalic acid-[(2,3-dihydroxy-N-methyl-propyl)-(2,3-dihydroxypropyl)]-diamide of Formula (I), is an iodine-containing X-ray contrast agent, and it has 3 bulky iodine atoms on the 2, 4, and 6 positions of the phenyl group, which sterically hinder the free rotation of the dihydroxypropyl-N-methylamino group, so that two atropisomer occur (M. Oki, *Topics in Stereochemistry*, volume 14, 1983, pp. 1~81; and H. Staab, et al., *Tetrahedron Letters*, No. 38, 1966, pp. 4593~4598).

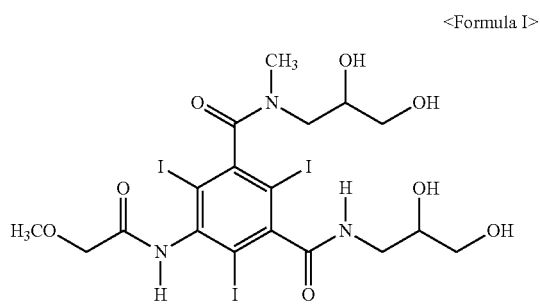 [SMILES: COCC(=O)Nc1c(I)c(C(=O)NCC(O)CO)c(I)c(C(=O)N(C)CC(O)CO)c1I]

<Formula I>

Besides the two atropisomers of Iopromide, there also exist E and Z isomers produced due to the steric hindrance of the free rotation between the carbon atom and nitrogen atoms of the amide bonds. Accordingly, iopromide is composed of a mixture of four isomers, and E1, E2, Z1 and Z2. In one of the atropisomers, the substituted nitrogen atom lies above the plane of the benzene ring of iopromide, while in the other, it lies below the plane of the benzene ring.

As shown in Formulae 2A and 2B, the E and Z forms can be distinguished by the arrangement of the substituents around C—N bond of the dihydroxy-N-methyl-proyl amide group.

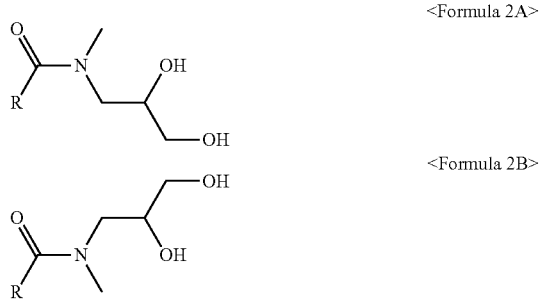

<Formula 2A>

<Formula 2B> wherein,
R is a phenyl group of iopromide.

These isomers have different physical properties and the relative amount of a singe isomer as well as the relative contents of the isomers is regulated in a pharmaceutical formulation. According to the *United States Pharmacopoeia, 31$^{st}$ Edition,* 2008, pp 2433-2435, a pharmaceutical raw material must contain 40 to 50% of form 1 isomer and 49 to 60% of form 2 isomer, and a medicinal product must contain 8.0 to 12.0% of E1 isomer, 9.0 to 14.0% E2 isomer, 32.0 to 40.0% of Z1 isomer, and 38.0 to 46.0% of Z2 isomer.

On the other hand, no effective method for crystallizing iopromide is currently available. U.S. Pat. No. 4,364,921 discloses a method for preparing iopromide, but, it does not employ a final crystallization step. Although European Patent EP 1,025,067 and English Patent GB 2,280,436 disclose a method for washing and crystallizing iopamidol and iodixanol, they do not teach any crystallization procedure for iopromide or iopromide isomers.

An injection formulation of iopromide can be prepared by dissolving a pharmaceutical raw material in water, adding pharmaceutically acceptable excipients to the solution, and sterilizing it, but, when a conventional iopromide raw material containing E and Z isomers is used to formulate a pharmaceutical product, the relative contents of the isomers in the product often do not meet the regulation.

International Publication No. WO 2007/065534 discloses a method for recovering iopromide suitable for pharmaceutical purposes from an iopromide solution. However, it merely teaches the isolation of form 1 and 2 isomers, and, therefore, it is difficult to selectively obtain Z isomer of iopromide.

The present inventors have found that a method for selectively resolving and crystallizing Z isomer of iopromide from crystalline iopromide or an iopromide concentrate containing E and Z isomers.

SUMMARY OF THE INVENTION

Accordingly, it is an object of the present invention to provide a high-yield method for selectively crystallizing Z isomer of iopromide from crude iopromide or a concentrate thereof containing a mixture of E and Z isomers.

It is another object of the present invention to provide a method for preparing a composition comprising Z isomer of iopromide obtained by the above crystallizing method.

In accordance with one aspect of the present invention, there is provided a method for selectively crystallizing Z isomer of iopromide comprising a) dissolving a crude iopromide or a concentrate thereof containing E and Z isomers in an alcohol; and b) heating the resulting alcohol solution to selectively obtain crystalline Z isomer of iopromide.

In accordance with another aspect of the present invention, there is provided a method for preparing a composition comprising Z isomer of iopromide comprising i) selectively crystallizing the Z isomer of iopromide from a crude crystal containing a mixture of E and Z isomers of iopromide or a concentrate thereof to obtain crystalline Z isomer of iopromide; and ii) dissolving the crystalline Z isomer of iopromide, together with a pharmaceutically acceptable excipient.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
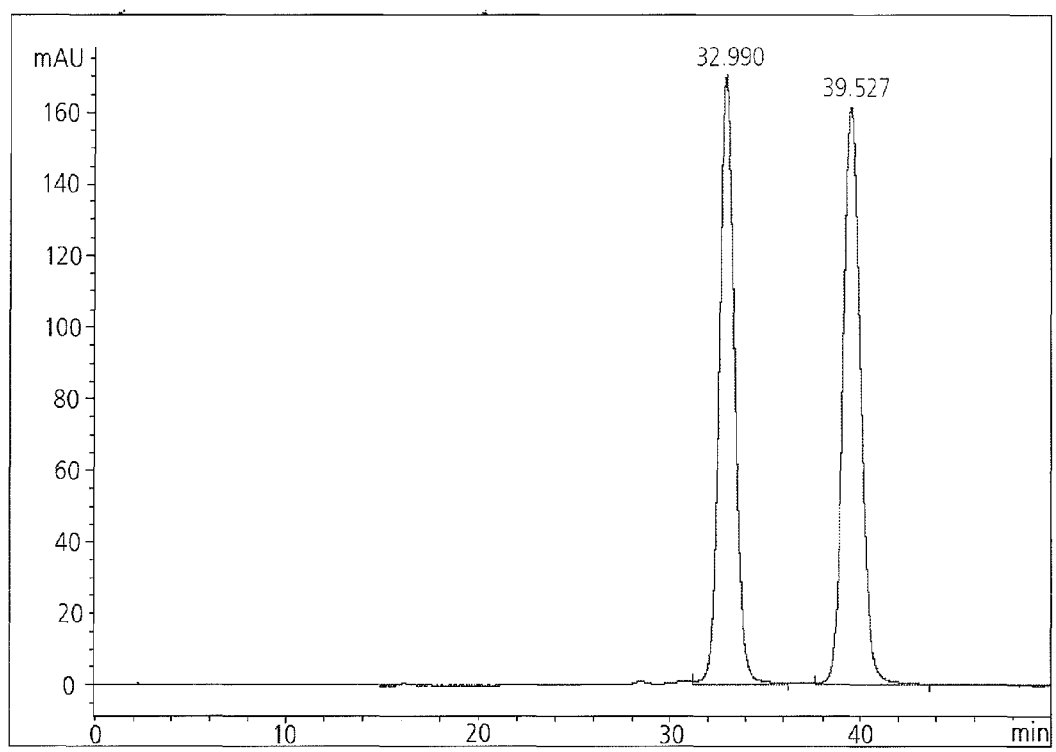
FIG. 1: a liquid chromatography scan of the inventive iopromide crystal containing the Z isomer obtained in Example 1.

In the present invention, there is provided a method for selectively crystallizing Z isomer of iopromide comprising a) dissolving a crude iopromide containing a mixture of E and Z isomers or a concentrate thereof in an alcohol; and b) heating the alcohol solution to selectively obtain crystalline Z isomer of iopromide.

As shown in Scheme 1, crude iopromide may be prepared by the method disclosed in U.S. Pat. No. 4,364,921:

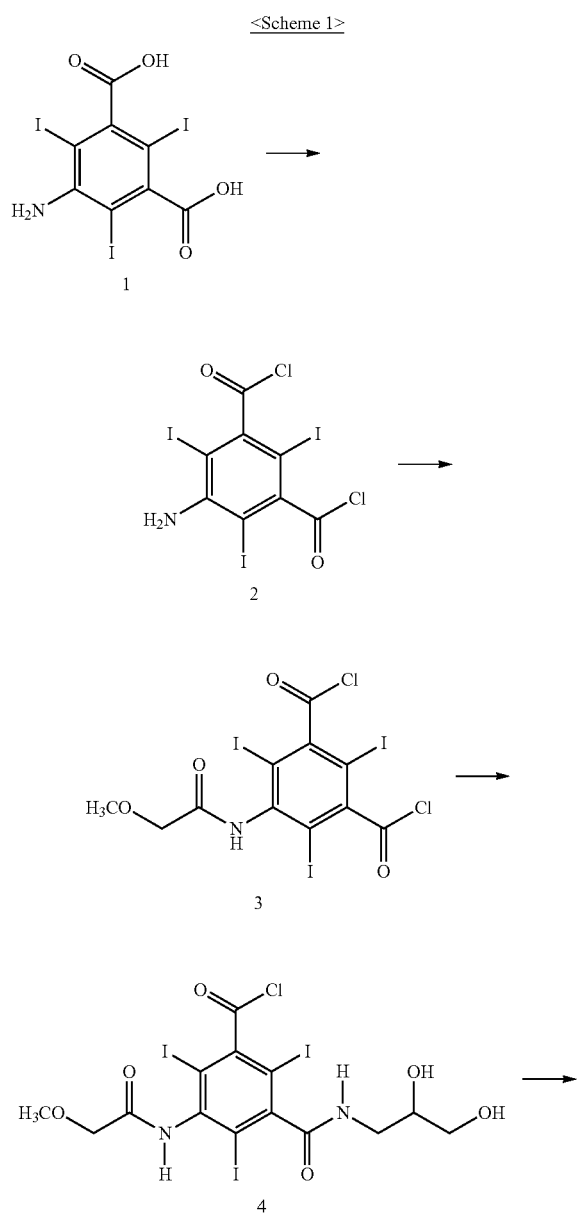

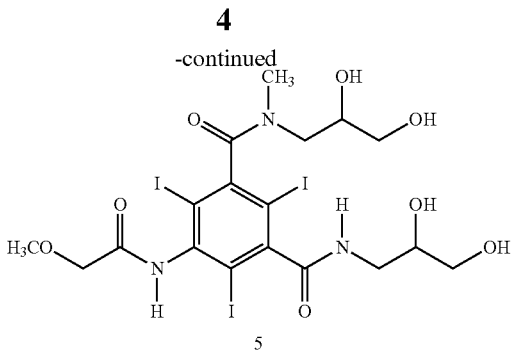

The crude iopromide or the concentrate thereof may contain 1:0.5 to 1:10 of E isomer:Z isomer, and 0 to 15 wt % of moisture.

In the step a) of the present invention, the volume (ml) of alcohol to be used for dissolving the crude crystal or the concentrate thereof is suitably from 0.1 to 10 times, preferably 1 to 3 times the weight (g) of the crude iopromide crystal or the concentrate thereof. The preferred alcohol as used herein is a $C_{1-10}$ straight or branched aliphatic alcohol, preferably, methanol, ethanol, isopropanol, n-butanol, sec-butanol, pentanol, octanol, decanol or a mixture thereof.

In the step b) of the present invention, heat treatment may be accomplished by various methods known in the art, preferably by heat refluxing. The Z isomer may be selectively crystallized by heat refluxing for 1 to 48 hours, while keeping the vessel's external temperature at 50 to 200° C., preferably, 80 to 180° C., more preferably, 100 to 150° C., under normal atmospheric pressure. The heat refluxing time can be modulated depending on an experimental scale, i.e., mass of the crude iopromide, and the above time range are intended to illustrate the present invention without limiting its scope.

The Z isomer content of the iopromide crystal obtained by the above method is preferably 85 to 100%, or the iopromide crystal may consist of 100% of Z form isomer or contain 5% or less of E form isomer.

When the crystallization is conducted by the method according to the present invention, the refluxing time can be shortened, and, therefore, a the amount of degradation products due to exposure to high temperature for a long time can be reduced.

In accordance with another aspect of the present invention, there is provided a method for preparing a composition comprising a Z isomer of iopromide comprising i) selectively crystallizing Z isomer of iopromide from crude iopromide comprising a mixture of E and Z isomers of iopromide or a concentrate thereof to obtain crystalline Z isomer of iopromide; and ii) dissolving the crystalline Z isomer of iopromide, together with a pharmaceutically acceptable excipient.

The crystallizing step i) in the above composition preparation method is characterized in comprising 1) dissolving crude iopromide or a concentrate thereof containing E and Z isomers in an alcohol; and 2) heating the resulting alcohol solution to obtain crystalline Z isomer of iopromide, and details of the preparation method are the same as those defined as the above crystallizing method for the Z isomer of iopromide.

A pH adjusting agent such as NaOH, and a stabilizing agent such as calcium disodium edetate may be used in the preparation method for a Z isomer-containing composition (see U.S. Pat. No. 4,634,921), and the aqueous solvent as used herein may be water.

The composition comprising the Z isomer of iopromide prepared by the above method may be sterilized and formulated in form of an injection formulation, and colorless and transparent liquid formulation is preferred.

With the Z isomer of iopromide-containing composition prepared by the method according to the present invention, a pharmaceutical raw material which renders the ratios of E1, E2, Z1, and Z2 isomers to be satisfied with the standards suitable for a pharmaceutical formulation such as those described in the USP. A ratio of form 1 isomer:form 2 isomer can be regarded as a ratio Z1 isomer:Z2 isomer, since the ratio of form 1 isomer:form 2 isomer generally refers to (E1+Z1): (E2+Z2), and the relative amounts of E1 to Z1 and E2 and Z2 are not regulated. In this regard, when adjusting the relative amounts of iopromide isomers in the raw pharmaceutical material based on Z1 and Z2 will be much easier to satisfy said standard with reproducibility.

The present invention will be described in further detail with reference to the following Examples. However, it should be understood that the present invention is not restricted by the specific Examples.

Example 1

Crystallization of Z Isomer Using Ethanol 10 g of 5-methoxyacetylamino-2,4,6-triiodo-isophthalic acid-[(2,3-dihydroxy-N-methyl-propyl)-(2,3-dihydroxypropyl)]-diamide containing 0.5 wt % of moisture (12.64 mmol) was synthesized by the method disclosed in U.S. Pat. No. 4,364,921. Further, the crude crystal prepared by said method was dissolved in 10 ml of anhydrous ethanol and the solution was refluxed while keeping the vessel's external temperature at 120° C. Then, the iopromide crystal of Z isomer farmed by refluxing for 6 hours, was cooled to room temperature, stirred for 1 hour, and filtered. The isolated solid crystal was washed with anhydrous ethanol cooled to 0 to 5, and dried at 80° C. under a reduced pressure, to obtain 9.5 g of the title compound (yield: 96%) as a white solid.

The isomer contents of the obtained crystal were determined by liquid chromatography using 4.6 mm×25 cm column (5 μm L1 packing) according to the method described in the *United States Phamacopoeia* (USP), and the results in FIG. 1 showed that the crystal was composed of 46.4% Z1 and 53.6% Z2 (Z isomer content: 100%).

Figure 2:
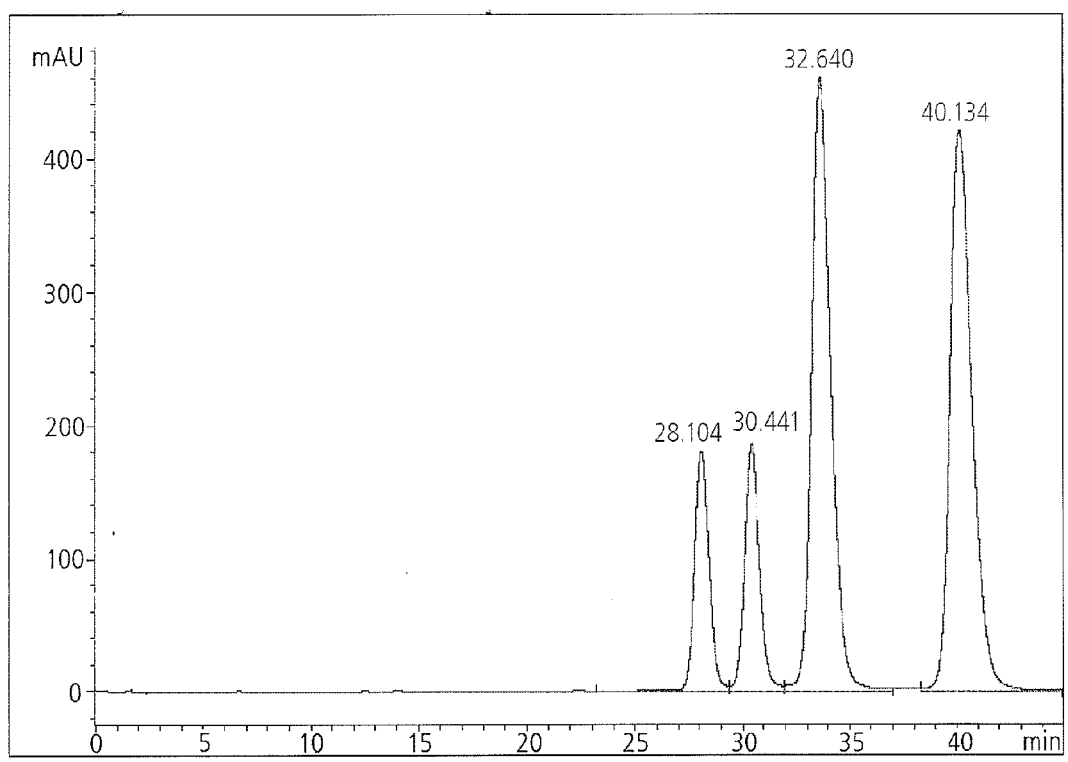
FIG. 2: a liquid chromatography scan of the crude iopromide crystal containing E and Z isomers.

Further, the crude crystal of iopromide prepared by the method disclosed in U.S. Pat. No. 4,364,921 was analyzed in the same manner as shown above, and the results are shown in FIG. 2.

Example 2

Crystallization of Z Isomer Using Ethanol 10 g of 5-methoxyacetylamino-2,4,6-triiodo-isophthalic acid-[(2,3-dihydroxy-N-methyl-propyl)-(2,3-dihydroxypropyl)]-diamide containing 3.0 wt % of moisture (12.64 mmol) was synthesized by the method disclosed in U.S. Pat. No. 4,364,921. Further, the crude crystal prepared by said method was dissolved in 10 ml of anhydrous ethanol and the solution was refluxed while keeping the vessel's external temperature at 120° C. Then, the iopromide crystal of Z isomer formed by refluxing for 6 hours, was cooled to room temperature, stirred for 1 hour, and filtered. The isolated solid crystal was washed with anhydrous ethanol cooled to 0 to 5, and dried at 80° C. under a reduced pressure, to obtain 9.5 g of the title compound (yield: 90%) as a white solid.

The isomer contents of the obtained crystal were determined in the same manner as in the above Example 1.

The isomer contents of the obtained crystal: 46.8% Z1, 53.2% Z2 (Z isomer content: 100%).

Example 3

Crystallization of Z Isomer Using Isopropyl Alcohol 10 g of 5-methoxyacetylamino-2,4,6-triiodo-isophthalic acid-[(2,3-dihydroxy-N-methyl-propyl)-(2,3-dihydroxypropyl)]-diamide containing 3.0 wt % of moisture (12.64 mmol) was synthesized by the method disclosed in U.S. Pat. No. 4,364,921. Further, the crude crystal prepared by said method was dissolved in 10 ml of isopropyl alcohol and the solution was refluxed while keeping the vessel's external temperature at 120° C. Then, the iopromide crystal of Z isomer formed by refluxing for 6 hours, was cooled to room temperature, stirred for 1 hour, and filtered. The isolated solid crystal was washed with isopropyl alcohol cooled to 0 to 5° C., and dried at 80° C. under a reduced pressure, to obtain 9.5 g of the title compound (yield: 95%) as a white solid.

The isomer contents of the obtained crystal were determined in the same manner as in the above Example 1.

The isomer contents of the obtained crystal: 45.5% Z1, 54.5% Z2 (Z isomer content: 100%).

Example 4

Crystallization of Z Isomer Using Methanol 10 g of 5-methoxyacetylamino-2,4,6-triiodo-isophthalic acid-[(2,3-dihydroxy-N-methyl-propyl)-(2,3-dihydroxypropyl)]-diamide containing 3.0 wt % of moisture (12.64 mmol) was synthesized by the method disclosed in U.S. Pat. No. 4,364,921. Further, the crude crystal prepared by said method was dissolved in 5 ml of isopropyl alcohol and the solution was refluxed while keeping the vessel's external temperature at 120° C. Then, the iopromide crystal of Z isomer formed by refluxing for 12 hours, was cooled to room temperature, stirred for 1 hour, and filtered. The isolated solid crystal was washed with isopropyl alcohol cooled to 0 to 5° C., and dried at 80° C. under a reduced pressure, to obtain 8.5 g of the title compound (yield: 85%) as a white solid.

The isomer contents of the obtained crystal were determined in the same manner as in the above Example 1.

The isomer contents of the obtained crystal: 47.6% Z1, 52.4% Z2 (Z isomer content: 100%).

Example 5

Crystallization of Z Isomer Using n-Butanol 10 g of 5-methoxyacetylamino-2,4,6-triiodo-isophthalic acid-[(2,3-dihydroxy-N-methyl-propyl)-(2,3-dihydroxypropyl)]-diamide containing 3.0 wt % of moisture (12.64 mmol) was synthesized by the method disclosed in U.S. Pat. No. 4,364,921. Further, the crude crystal prepared by said method was dissolved in 10 ml of butanol and the solution was refluxed while keeping the vessel's external temperature at 120° C. Then, the isopromide crystal of Z isomer formed by refluxing for 6 hours, was cooled to room temperature, stirred for 1 hour, and filtered. The filtered solid crystal was washed with n-butanol cooled to 0 to 5° C., and dried at 80° C. under a reduced pressure, to obtain 9.5 g of the title compound (yield: 95%) as a white solid.

The isomer contents of the obtained crystal were determined in the same manner as in the above Example 1.

The isomer contents of the obtained crystal: 48.3% Z1, 51.7% Z2 (Z isomer contents: 100%).

The amounts of free iodide and residual solvent of each of the iopromide crystals obtained in Examples 1 to 5 were determined according to the method described in the *United States Pharmacopoeia* 31$^{st}$ *edition* using a potentiometric titrator and gas chromatography as they were compared with the standard concentrate limits described in the USP and ICH (International Conference on Harmonization) guideline. The results are shown in Table 1. The standard concentrate limits of residual solvents for methanol (MeOH), isopropyl alcohol (IPA) and n-butanol (n-BuOH) were calculated based on the Permitted Daily Exposure (PDE), described in ICH guideline, and standard concentrate limit of residual ethanol (EtOH) was calculated based on the PDE described in the USP. The methods for the calculating standard concentrate limits of residual solvents with PDE are as follows:

1) Maximum daily dose of iopromide (Ultravist™ 370, based on FDA standard): (769 mg/ml)×225 ml=173.025 g/day
2) Reference concentrate limits of residual solvent (ppm) =(1000×PDE)/daily dose
   i) MeOH (ppm)=(1000×30 mg/day)/(173.025 g/day) =173.38 ppm
   ii) IPA (ppm)=(1000×50 mg/day)/(173.025 g/day) =288.976 ppm
   iii) n-BuOH (ppm)=(1000×50 mg/day)/(173.025 g/day) =288.976 ppm

TABLE 1

| Example | Amount of free iodine (Standard amount: 0.002%; USP) | Residual solvents Standard value | Measured value |
|---|---|---|---|
| 1 | 0.000099% | EtOH 4000 ppm (USP) | EtOH 35 ppm |
| 2 | 0.0001765% | EtOH 4000 ppm (USP) | EtOH 51 ppm |
| 3 | 0.0004524% | IPA 288.98 ppm (PDE 50 mg/day) | IPA 55 ppm |
| 4 | 0.0003476% | MeOH 173.38 ppm (PDE 30 mg/day) | MeOH 63 ppm |
| 5 | 0.000241% | n-BuOH 288.98 ppm (PDE 50 mg/day) | n-BuOH 44 ppm |

As can be seen from the above Table 1, the iopromide crystal prepared by the method according to the present invention satisfied the standards described in the USP and ICH guideline, and the method according to the present invention has superior effects over the conventional methods in terms of shortening the refluxing time and reducing the amount of degradation products.

Test Example 1

Preparation of a Pharmaceutical Formulation and Ratios of Isomers in the Formulation 62.34 g of Iopromide crystal containing only Z isomer prepared in Example 1 (Z1 isomer 46.4% and Z2 isomer 53.6%) was dissolved in 0.01 g of calcium edetate and 100 ml of secondary distilled water, and then, pH of the solution was adjusted with 0.1N NaOH to 7.2. The solution was poured into a container and sterilized for 20 minutes at 120° C. to prepare a pharmaceutical formulation. As shown in Table 2, the relative amounts of the iopromide isomers in the formulation satisfied the standards described in the USP.

Comparative Example

A pharmaceutical formulation was prepared with 62.34 g of iopromide crystal (E1 isomer 8.76%, E2 isomer 10.60%, Z1 isomer 39.68% and Z2 isomer 40.97%) in the same manner as in the above Test Example 1. Then the ratios of iopromide isomers in the formation were analyzed. As shown in Table 2, the relative amounts of the iopromide isomers in the formulation do not satisfied the standards described in the USP.

TABLE 2

| | E1 | E2 | Z1 | Z2 |
|---|---|---|---|---|
| Standard amount ratio (USP) | 8.0 to 12.0% | 9.0 to 14.0% | 32.0 to 40.0% | 38.0 to 46.0% |
| Test Example 1 | 9.11% | 10.5% | 38.64% | 41.7% |
| Comparative Example 1 | 12.41% | 14.42% | 35.10% | 38.07% |

While the invention has been described with respect to the above specific embodiments, it should be recognized that various modifications and changes may be made to the invention by those skilled in the art which also fall within the scope of the invention as defined by the appended claims.

What is claimed is:

1. A method for selectively crystallizing Z isomer of iopromide represented by the following formula (I):

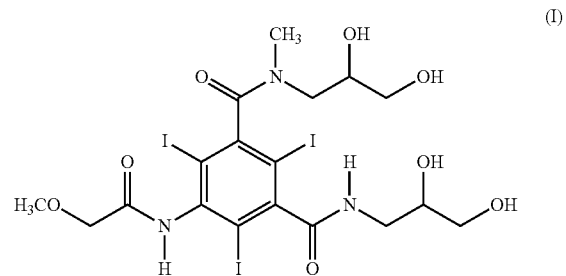 [SMILES: COCC(=O)Nc1c(I)c(C(=O)NCC(O)CO)c(I)c(C(=O)N(C)CC(O)CO)c1I]

said method comprising:
a) dissolving crude iopromide or a concentrate thereof containing E and Z form isomers in an alcohol; and
b) heating the resulting alcohol solution of the crude iopromide or the concentrate at a temperature ranging from 80° C. to 180° C. for 6-48 hours to obtain a crystalline iopromide comprising Z form isomer in an amount of 85-100% based on the total amount of the crystalline Z isomer of iopromide.

2. The method of claim 1, wherein the content of Z isomer of iopromide crystal obtained in step b) ranges from 95% to 100%.

3. The method of claim 1, wherein the alcohol is a straight or branched $C_{1-9}$ aliphatic alcohol.

4. The method of claim 1, wherein the volume (ml) of the alcohol is 0.1 to 10 times the weight (g) of the crude iopromide crystal or the concentrate thereof.

5. The method of claim 1, wherein the E isomer to Z isomer ratio of in the crude iopromide or the concentrate thereof ranges from 1:0.5 to 1:10.

6. The method of claim 1, wherein the moisture content of the crude crystal or the concentrate thereof ranges from 0 wt % to 15 wt %.

7. A method for preparing a composition comprising Z isomer of iopromide of the following formula (I) comprising
a) dissolving crude iopromide or a concentrate thereof containing E and Z form isomers in an alcohol;
b) heating the resulting alcohol solution of the crude iopromide or the concentrate at a temperature ranging from 80° C. to 180° C. for 6-48 hours to obtain a crystalline iopromide comprising Z form isomer in an amount of 85-100% based on the total amount of the crystalline iopromide; and
c) dissolving the crystalline iopromide in a solvent, together with a pharmaceutically acceptable excipient to give a composition comprising 32-40 wt % of Z1 isomer of iopromide and 38-46 wt % of Z2 isomer of iopromide,

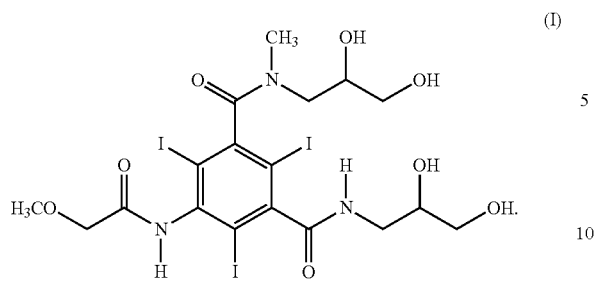

(I)

8. The method of claim 7, wherein the content of Z isomer of iopromide of the crystal ranges from 95% to 100%.

9. The method of claim 7, wherein the alcohol is a straight or branched $C_{1-10}$ aliphatic alcohol.

10. The method of claim 7, wherein the volume (ml) of the alcohol is 0.1 to 10 times weight (g) of the crude iopromide crystal or the concentrate thereof.

11. The method of claim 7, wherein the ratio of E isomer to Z isomer ratio of in the crude iopromide or the concentrates thereof ranges from 1:0.5 to 1:10.

12. The method of claim 7, wherein the moisture content of the crude crystal or the concentrate thereof ranges from 0 wt % to 15 wt %.

* * * * *